United States Patent
Chen

[11] Patent Number: 6,090,994
[45] Date of Patent: Jul. 18, 2000

[54] STRUCTURE OF A DIAPER

[76] Inventor: Chuan-Mei Chen, P.O.Box 82-144, Taipei, Taiwan

[21] Appl. No.: 09/178,560

[22] Filed: Oct. 26, 1998

[51] Int. Cl.$^7$ .................................................. A61F 13/15
[52] U.S. Cl. .............. 604/378; 604/385.01; 604/385.101
[58] Field of Search ................. 604/385.01, 385.03, 604/385.04, 385.12, 385.201, 385.21, 385.23, 385.101

[56] References Cited

U.S. PATENT DOCUMENTS

| | | | |
|---|---|---|---|
| 4,055,180 | 10/1977 | Karami | 604/385.01 |
| 4,643,727 | 2/1987 | Rosenbaum | 604/378 |
| 4,723,953 | 2/1988 | Rosenbaum et al. | 604/378 |
| 4,865,597 | 9/1989 | Mason, Jr. et al. | 604/385.01 |
| 5,643,238 | 7/1997 | Baker | 604/378 |

Primary Examiner—John G. Weiss
Assistant Examiner—Dennis Ruhl
Attorney, Agent, or Firm—A&J

[57] ABSTRACT

A diaper includes an outer layer, a ventilating layer made of resilient material and mounted on an inner side of the otuer layer, the ventilating layer having an outer frame, a plurality of convex cross-shaped ribs each enclosed with a circular edge, and a plurality of elongated ribs joining adjacent circular edges of the convex cross-shaped ribs and the outer frame together, absorbent layer arranged on the ventilating layer, and a permeable layer made of non-woven fabric and disposed on the absorbent layer, whereby the diaper is of good ventilation and can prevent liquid discharge from leaking out thereof.

3 Claims, 5 Drawing Sheets 6,090,994

STRUCTURE OF A DIAPER

BACKGROUND OF THE INVENTION

1. Field of the Invention

This invention is related to the structure of a diaper and in particular to one which is of good ventilation and does not wrinkle.

2. Description of the Prior Art

The conventional diaper generally includes a water-proof outer layer made for PE (polyethylene), a permeable layer made of non-woven fabric, and an absorbent layer fitted between the outer layer and the permeable layer. However, as the absorbent layer is primarily made of fiber paper pulp and so the fiber paper pulp will become loose or even form a plurality of lumps which will let out liquid discharge subject to pressure. Hence, it has been proposed to provide two leak-proof flaps at two sides of a diaper in order to prevent the liquid discharge from leaking out thereof, but when there is a large amount of liquid discharge in a short time, some of the liquid discharge will still leak out of the diaper. As concerns ventilation, it has been proposed to utilize ventilation property of the absorbent layer and foam sponge at the front and rear waist portions to achieve the ventilating purpose. Nevertheless, if the diaper is tightly bound around the waist, the outlet of the foam sponge will be closed thereby influencing the effect of ventilation and often causing skin diseases.

Therefore, it is an object of the present invention to provide an improvement in the structure of a diaper which can obviate and mitigate the above-mentioned drawbacks.

SUMMARY OF THE INVENTION

This invention is related to an improvement in the structure of a diaper.

It is the primary object of the present invention to provide an improved diaper which is of good ventilation.

It is another object of the present invention to provide an improved diaper which does not wrinkle.

It is still another object of the present invention to provide an improved diaper which can be used as a mattress for therapy.

It is still another object of the present invention to provide an improved diaper which can prevent urine from leaking out therefrom.

It is a further object of the present invention to provide an improved diaper which can make a user feel fine and comfortable.

The foregoing objects and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENT

Figure 1:
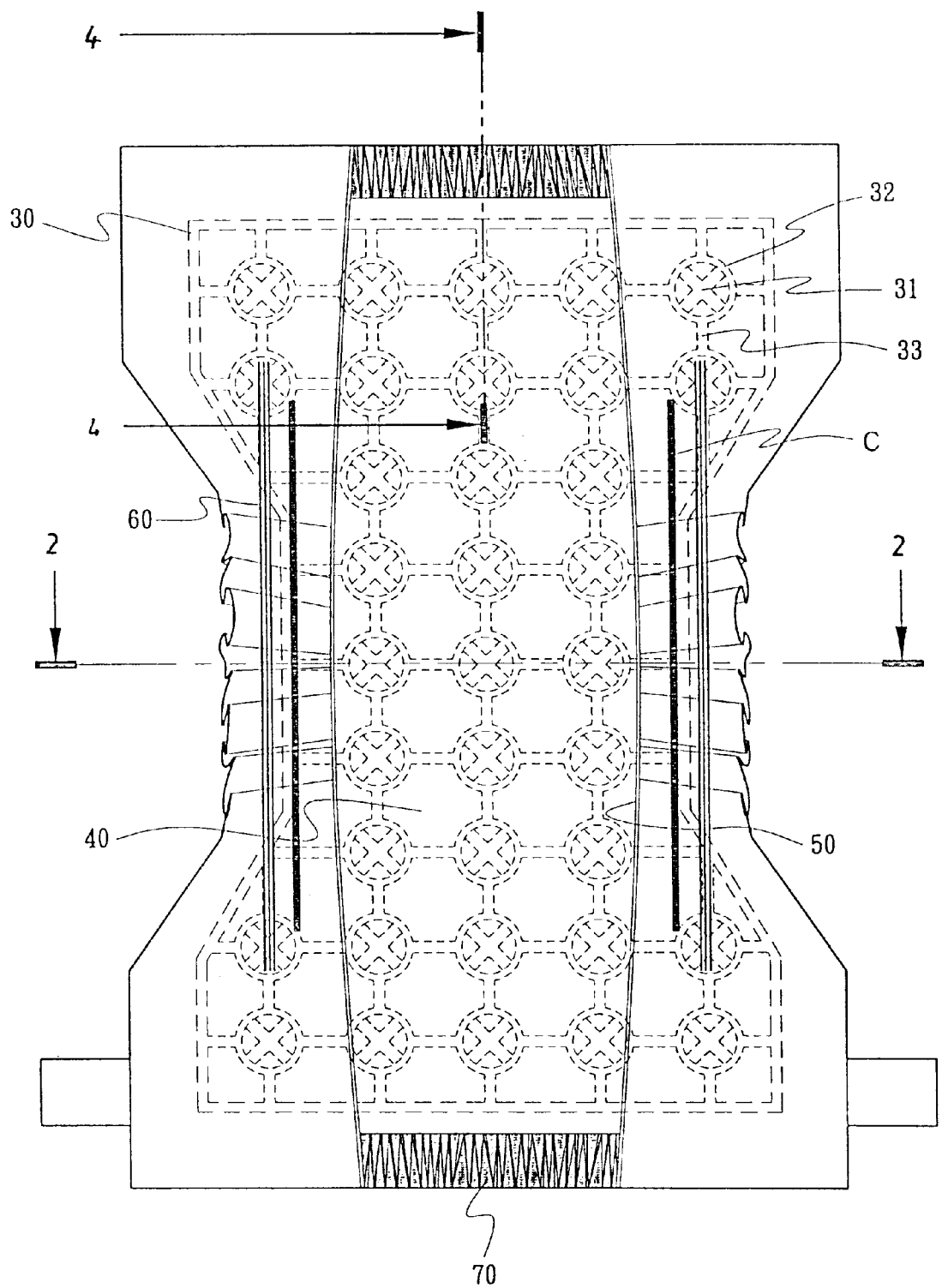
FIG. 1 is a developed view of a diaper according to the present invention.

For the purpose of promoting an understanding of the principles of the invention, reference will now be made to the embodiment illustrated in the drawings. Specific language will be used to describe same. It will, nevertheless, be understood that no limitation of the scope of the invention is thereby intended, such alterations and further modifications in the illustrated device, and such further applications of the principles of the invention as illustrated herein being contemplated as would normally occur to one skilled in the art to which the invention relates.

Figure 2:
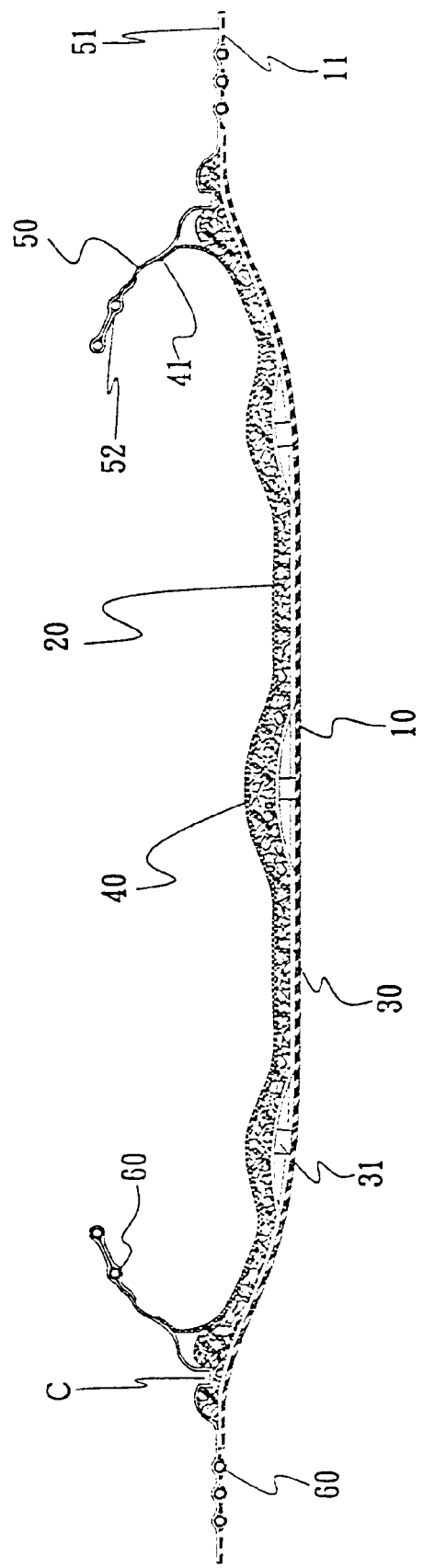
FIG. 2 is a sectional view taken along line 2—2 of FIG. 1.
Figure 5:
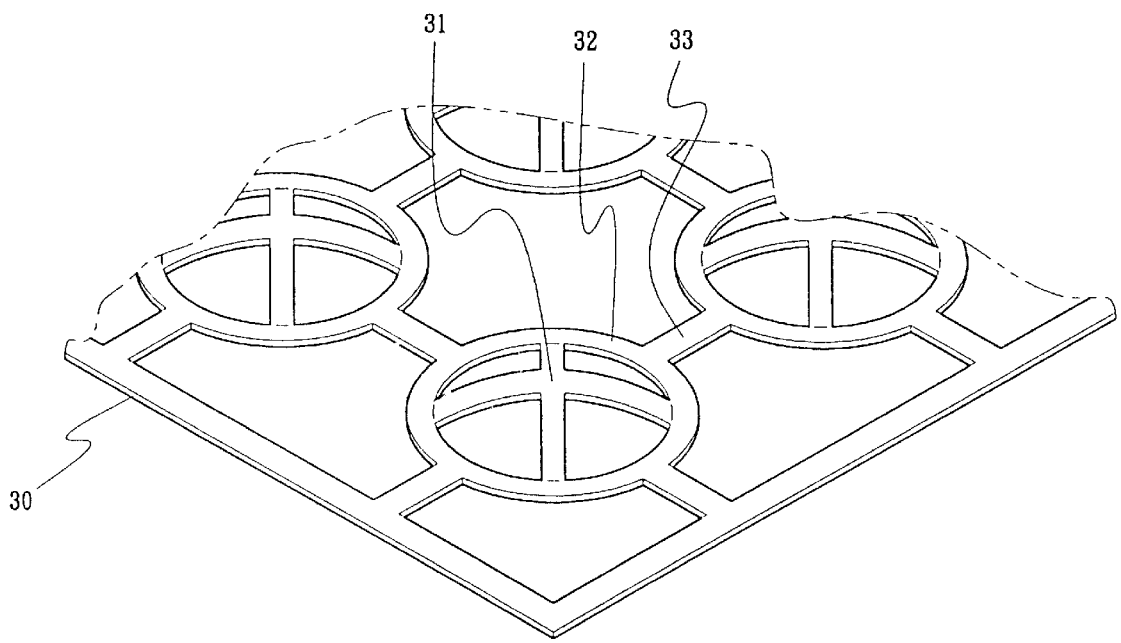
FIG. 5 illustrates the structure of the ventilating layer.

With reference to the drawings and in particular to FIGS. 1 and 2 thereof, the diaper according to the present invention generally comprises an outer layer 10 made of PE (polyethylene), an ventilating layer 30 made of resilient material and mounted on an inner side of the outer layer 10, an absorbent layer 20 arranged on the ventilating layer 30, and a permeable layer 40 made of non-woven fabric and disposed on the absorbent layer 20. The ventilating layer 30 is made of resilient material and has an outer frame provided with a plurality of convex cross-shaped ribs 31 each enclosed with a circular edge (see FIG. 5). The convex cross-shaped ribs 31 are joined together and to the outer frame of the ventilating layer 30 by elongated ribs 33. The ventilating layer 30, the absorbent layer 20 and the permeable layer 40 are closedly engaged with the outer layer 10 so that the inner surface of the diaper will be formed with a plurality of circular convex portions. Each longitudinal outer side portion 11 of the outer layer 10 is joined to a longitudinal outer side portion 51 of a leak-proof flap 50, with a plurality of elongated resilient elements 60 fitted therebetween. The longitudinal inner side portion 52 of the leak-proof flap 50 is affixed to a longitudinal side portion 41 of the permeable layer 40, with a plurality of elongated resilient elements 60 therebetween. By means of the leak-proof flaps 50, the absorbent layer 20 can be completely enclosed by the permeable layer 40 and the outer layer 10. Further, the leak-proof flap 50 is formed with a groove C extending into the absorbent layer 20.

Figure 3:
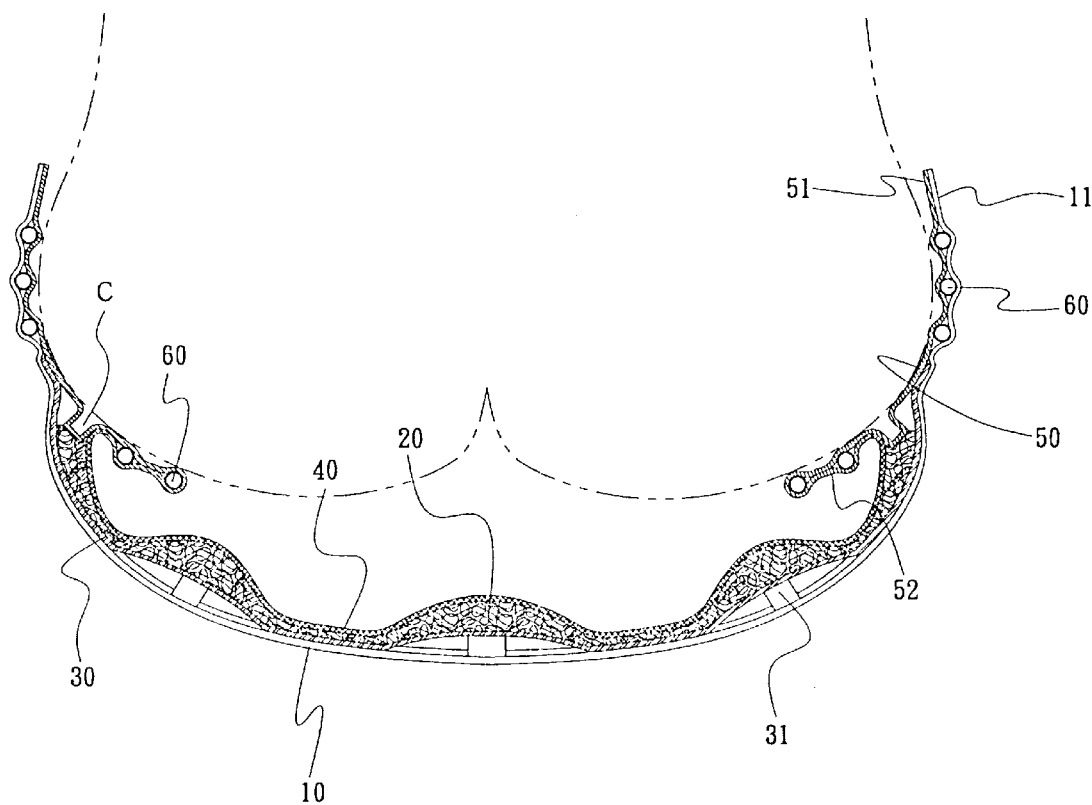
FIG. 3 is a sectional view of the present invention.

Referring to FIG. 3, the longitudinal outer side portion 51 of the leak-proof flap 50 and the longitudinal outer side portion 11 of the outer layer 10 can be used for wrapping the hip of an user as shown. By means of the longitudinal inner side portion 52 of the leak-proof flap 50, the liquid discharge will be effectively guided to the absorbent layer 20 without worrying the liquid discharge to leak outside. If the liquid discharge is momentarily increased, it will be guided through the groove C to the other portion of the absorbent layer 20 so that every portion of the absorbent layer 20 can be fully utilized. In addition, when the user wearing the diaper moves his hip, the permeable layer 40, the absorbent layer 20 and the ventilating layer 30 will force the air inside the convex cross-shaped ribs 31 to flow out of the diaper thereby causing air ventilation and dissipating the heat inside the diaper. Hence, the diaper can be always kept dry thereby preventing skin diseases.

Figure 4:
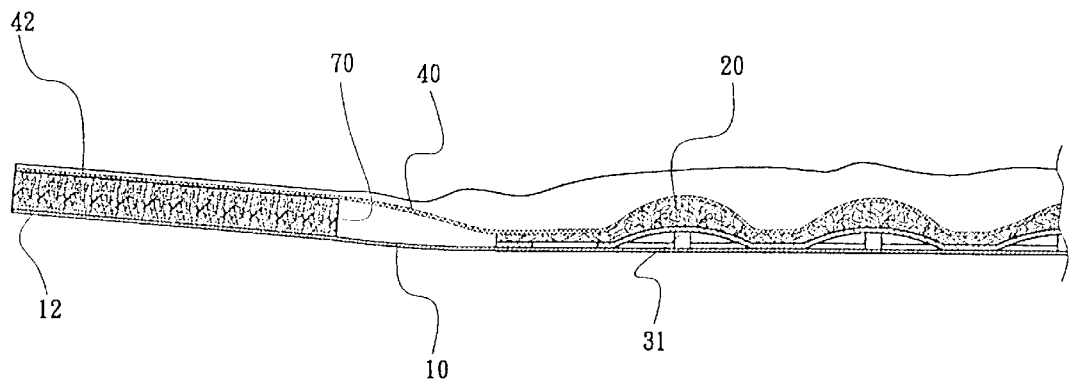
FIG. 4 is a sectional view taken along line 4—4 of FIG. 1.

Turning now to FIGS. 1 and 4, a sponge 70 is fitted between the transverse outer edge 12 of the outer lager 10 and the transverse side portion 42 of the permeable layer 40, so that when the convex cross-shaped ribs 31 are depressed, the air inside the convex cross-shaped ribs 31 will be ejected out of the diaper through the sponge 70.

Figure 6:
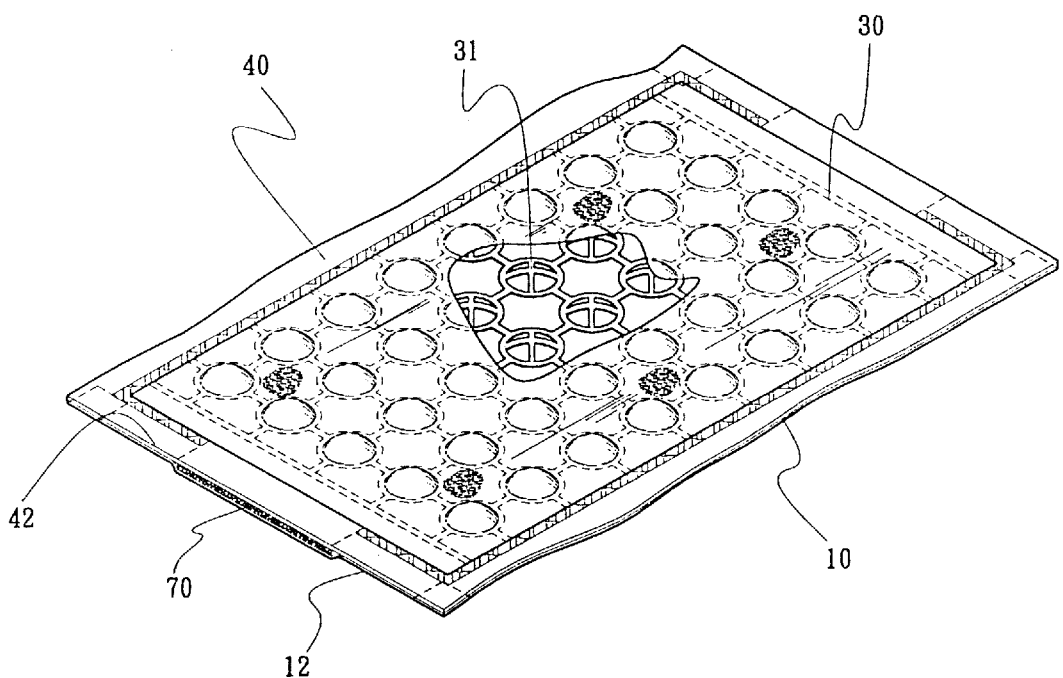
FIG. 6 illustrates another preferred embodiment of the present invention.

Furthermore, the diaper may be used as a mattress for therapy. As shown in FIGS. 4 and 6, the ventilating layer 30 with convex cross-shaped ribs 31 is fitted between the outer layer 30 and the absorbent layer 20 coated with a sheet of non-woven fabric 40, thereby forming a plurality of circular protrusions on the surface of the diaper. The sponge 70 is fitted between the outer edge 12 of the outer lager 10 and the outer edge 42 of the permeable layer 40, so that when a patient lies on the mattress, there will be clearances between the patient and the mattress hence enabling air to pass therethrough, and when the patient change his posture, the convex cross-shaped ribs 31 are depressed, the air inside the convex cross-shaped ribs 31 will be ejected out of the diaper through the sponge 70 thereby providing forced ventilation of air and therefore providing a fine and comfortable mattress for the patient.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. A diaper comprising:

an outer layer;

a ventilating layer made of resilient material and mounted on an inner side of said outer layer, said ventilating layer having an outer frame, a plurality of convex cross-shaped ribs each enclosed with a circular edge, and a plurality of elongated ribs joining adjacent circular edges of said convex cross-shaped ribs and said outer frame together;

absorbent layer arranged on said ventilating layer; and a permeable layer made of non-woven fabric and disposed on said absorbent layer;

whereby said diaper is formed with a plurality of raised circular convex portions.

2. The diaper as claimed in claim 1, further comprising two leak-proof flaps each having a longitudinal outer side portion secured to a longitudinal outer side portion of said outer layer and a longitudinal inner portion secured to a longitudinal side portion of said permeable layer thereby forming a groove extending into said absorbent layer.

3. The diaper as claimed in claim 1, further comprising two sponges each fitted between a transverse outer side portion of said outer layer and a transverse side portion of said permeable layer.

* * * * *